US011400029B2

(12) United States Patent
Kawata et al.

(10) Patent No.: US 11,400,029 B2
(45) Date of Patent: Aug. 2, 2022

(54) DENTAL PORCELAIN PASTE SUPERIOR IN APPLICATION PROPERTY

(71) Applicant: SHOFU INC., Kyoto (JP)

(72) Inventors: Keita Kawata, Kyoto (JP); Kenji Kono, Kyoto (JP)

(73) Assignee: SHOFU INC., Kyoto (JP)

( * ) Notice: Subject to any disclaimer, the term of this patent is extended or adjusted under 35 U.S.C. 154(b) by 176 days.

(21) Appl. No.: 16/749,005

(22) Filed: Jan. 22, 2020

(65) Prior Publication Data

US 2020/0330331 A1 Oct. 22, 2020

(30) Foreign Application Priority Data

Jan. 23, 2019 (JP) ............................ JP2019-009167

(51) Int. Cl.

| | |
|---|---|
| ***A61K 6/836*** | (2020.01) |
| ***A61K 6/65*** | (2020.01) |
| ***A61K 6/853*** | (2020.01) |
| ***A61K 6/78*** | (2020.01) |
| ***A61K 6/17*** | (2020.01) |
| ***A61K 6/76*** | (2020.01) |
| ***A61K 6/833*** | (2020.01) |
| ***C03C 8/16*** | (2006.01) |
| ***C03C 8/14*** | (2006.01) |
| ***C03C 14/00*** | (2006.01) |
| ***C03C 1/04*** | (2006.01) |

(52) U.S. Cl.

CPC ................ *A61K 6/836* (2020.01); *A61K 6/17* (2020.01); *A61K 6/65* (2020.01); *A61K 6/76* (2020.01); *A61K 6/78* (2020.01); *A61K 6/833* (2020.01); *A61K 6/853* (2020.01); *C03C 1/04* (2013.01); *C03C 8/14* (2013.01); *C03C 8/16* (2013.01); *C03C 14/004* (2013.01); *C03C 2204/00* (2013.01); *C03C 2205/06* (2013.01); *C03C 2214/04* (2013.01); *C04B 2235/3418* (2013.01); *C04B 2235/36* (2013.01); *C04B 2235/5436* (2013.01); *C04B 2235/5454* (2013.01); *C04B 2235/9646* (2013.01)

(58) Field of Classification Search

CPC . A61K 6/836; A61K 6/65; A61K 6/78; A61K 6/17; A61K 6/833; C03C 1/04; C03C 8/14; C03C 8/16; C03C 14/004; C03C 2205/06; C03C 2204/00; C03C 2214/04

See application file for complete search history.

(56) References Cited

U.S. PATENT DOCUMENTS

| | | | |
|---|---|---|---|
| 4,557,691 | A | 12/1985 | Martin et al. |
| 4,806,383 | A | 2/1989 | Poltz |
| 6,022,819 | A | 2/2000 | Panzera et al. |
| 6,444,597 | B1 | 9/2002 | Sato et al. |

FOREIGN PATENT DOCUMENTS

| | | | |
|---|---|---|---|
| DE | 10 2010 034 194 | | 2/2012 |
| JP | 59-196807 | | 11/1984 |
| JP | 01-125312 | | 5/1989 |
| JP | 2001-079019 | | 3/2001 |
| JP | 2017-193492 | | 10/2017 |
| WO | WO 2020/049392 | * | 3/2020 |
| WO | WO 2020/049393 | * | 3/2020 |

OTHER PUBLICATIONS

Extended European Search Report issued Sep. 8, 2020, in corresponding European Patent Application No. 20153032.6.

Evonik, "AEROSILE®-Fumed Silica: Technical Overview", Evonik Industiies, 2015.

* cited by examiner

*Primary Examiner* — C Melissa Koslow

(74) *Attorney, Agent, or Firm* — Wenderoth, Lind & Ponack, L.L.P.

(57) ABSTRACT

To provide a dental porcelain paste which can maintain maintaining the paste state and have excellent application property for a long period of time and hardly causes carbonization or bubbles due to the influence of an organic component or a polymer component during firing. The present invention provides a dental porcelain paste for preparing a dental prosthesis device, comprising: 50.0 to 80.0 wt. % of a glass powder (a) having a maximum particle diameter of 100 μm or less and an average particle diameter of 1 to 20 μm, 0.5 to 10.0 wt. % of a hydrophobized fine particle silica (b) having an average primary particle diameter of 1 to 50 nm, and 10.0 to 49.5 wt. % of an organic solvent (c) having a boiling point it is within (bp) of 100 to 300° C.

2 Claims, No Drawings

DENTAL PORCELAIN PASTE SUPERIOR IN APPLICATION PROPERTY

CROSS-REFERENCE TO RELATED APPLICATIONS

This application is based on and claims the benefit of priority from Japanese Patent Application Serial No. 2019-9167 (filed on Jan. 23, 2019), the contents of which are hereby incorporated by reference in their entirety.

BACKGROUND OF THE INVENTION

Field of the Invention

The present invention relates to a dental porcelain paste which is used for preparing a dental prosthesis device such as an artificial tooth and is a paste of a dental porcelain material or a coloring material for dental ceramics which are preferably used in building up a porcelain material manually by a dental technician.

Description of the Related Art

A dental porcelain material is a glass ceramics material comprising feldspar and the like as a raw material and is mainly used for a crown prosthesis restoration of a missing tooth. The dental porcelain material is classified by method of use into a metal bonding porcelain material which is baked on a metal frame for use, a zirconia porcelain material baked on a zirconia frame for use and a prosthesis device which is prepared from only a dental porcelain material.

A dental ceramics coloring material comprises a glass material or a glass ceramics material as a base material same as the dental porcelain material and is compounded with a various coloring material ingredient (pigment). The dental ceramics coloring material is used for a color tone adjustment of a dental porcelain material and a dental ceramics material (alumina and zirconia, etc.).

Patent Document 1 discloses a paste suitable for use in a dental coping as an opaque porcelain. The paste consists of an opaque porcelain material and a water-soluble colloidal dispersion of a urethane polymer.

The feature is that it is not necessary to fire before building up a body porcelain layer by forming a paste with a water-soluble colloidal dispersion of the urethane polymer.

However, it is not possible to completely incinerate the urethane polymer under the porcelain firing conditions and carbonization and bubbles are generated.

Patent Document 2 discloses an opaque ceramic paste which is prepared by mixing a ceramic powder containing about 10 to 20% of particles having a diameter less than about 2 μm and an organic solvent having a boiling point of less than 300° C.

However, it is difficult for this opaque ceramic paste to suppress separation of the powder component and the liquid component due to aged deterioration while maintaining excellent application property.

Patent Document 3 discloses a dental pasty porcelain material which is hardly dried and solidified during use. The feature of this dental pasty porcelain material is that the dental porcelain paste comprises a mixture of from 7 to 45 parts by weight of an organic solvent which has a viscosity of 50,000 to 1,500,000 cps and contains a dissolved polymer material, and a porcelain powder as a remainder, with a total amount being 100 parts by weight, and has a paste-like state.

However, because the high viscosity organic solvent containing the dissolved polymer material is used, it is not possible to completely incinerate in firing the porcelain material and carbonization and bubbles are generated. Further, it is difficult to uniformly apply in this technique.

Patent Document 4 discloses a pasty dental porcelain material that can suppress the color difference between before and after firing. The feature of this dental pasty dental porcelain material is that the dental pasty dental porcelain material contains a colorant that is decolorized during the firing, an organic solvent and a surface-treated porcelain material powder.

However, it is not possible to completely incinerate in firing and carbonization and bubbles are generated, in this technique. Further, it is difficult to uniformly apply.

None of the prior arts could achieve the suppression of carbonization and bubbles due to the unburned residue of the organic component and the polymer component during firing while maintaining the paste state having excellent application property for a long period of time.

RELEVANT REFERENCES

Patent Literature

[Patent document 1] Japanese Unexamined Patent Application Publication No. S59-196807

[Patent document 2] Japanese Unexamined Patent Application Publication No. H01-125312

[Patent document 3] Japanese Unexamined Patent Application Publication No. 2001-079019

[Patent document 4] Japanese Unexamined Patent Application Publication No. 2017-193492

SUMMARY OF THE INVENTION

Technical Problem

An object of the present invention is to provide a dental porcelain paste which can maintain maintaining the paste state for a long period of time and have excellent application property for a long period of time and hardly causes carbonization or bubbles due to the influence of an organic component or a polymer component during firing.

Solution to Problem

The dental porcelain paste of the present invention is a dental porcelain paste for preparing a dental prosthesis device, comprising: 50.0 to 80.0 wt. % of a glass powder (a) having a maximum particle diameter of 100 μm or less and an average particle diameter of 1 to 20 μm, 0.5 to 10.0 wt. % of a hydrophobized fine particle silica (b) having an average primary particle diameter of 1 to 50 nm, and 10.0 to 49.5 wt. % of an organic solvent (c) having a boiling point (bp) of 100 to 300° C.

In the present invention, the maximum particle diameter means a diameter of the largest particle among all particles. The maximum particle diameter of the glass powder can be determined by measurement using a laser diffraction scattering method, a dynamic light scattering method, a centrifugal sedimentation method, an electrical sensing zone method, or the like.

In the present invention, the average particle diameter means an average value of all particle diameters. The average particle diameter of the glass powder can be determined by measurement using a laser diffraction scattering method, a dynamic light scattering method, a centrifugal sedimentation method, an electrical sensing zone method, or the like.

In the present invention, the average primary particle diameter means an average value of all particle diameters in a state where they are not aggregated. The average primary particle diameter of fine particle silica can be calculated from the specific surface area obtained by measurement using a gas absorption method, a mercury intrusion method, a gas permeation method, a bubble point method, or the like.

In the present invention, it is preferable to further comprise a coloring material (d) and/or a fluorescent material (e).

Advantageous Effects of Invention

The dental porcelain paste of the present invention can be applied uniformly regardless of the skill of the technician, can maintain a constant paste property for a long period of time, can prevent carbonization and can suppress the generation of bubbles.

DETAILED DESCRIPTION OF THE PREFERRED EMBODIMENTS

In a dental porcelain paste, it is possible to obtain the desired shape of the dental prosthetic device by building up a dental porcelain paste on the core and firing it.

Generally, firing temperature for firing a dental porcelain paste is within a temperature range of 650° C. to 850° C. A dental porcelain paste is usually fired by holding for 1 to 10 minutes at this firing temperature.

When firing temperature is higher than 850° C., there is a case where a shape of the dental prosthesis device is not maintained and deformation and/or bubbles generate.

When the firing temperature is lower than 650° C., there is a case where the firing is not sufficient and carbonization occurs, and therefore desired color tone is not obtained. Further, because it requires long holding time of 10 minutes or more, there is a case where it is difficult to actually use.

In the present invention, one or more times of firings means firing at least once, there is a case where firing at the above firing temperature before forming the target shape of the dental prosthesis device is carried out and thereafter building up and further firing a dental porcelain paste is carried out, and it is possible to fire at the firing temperature a plurality of times.

The glass powder (a) is a glass component that serves as a base material for a dental prosthesis device obtained by firing and is melted and fused and bonded to the core material by firing. In the present invention, it is preferable that no glass powder other than the glass powder (a) is contained.

The average particle diameter of the glass powder is within a range of 1 to 20 μm. It is preferably within a range of 2 to 10 μm. Most preferably, it is within a range of 3 to 9 μm. When the average particle diameter is small, the glass particles may aggregate with each other in forming a paste, and the application property may be changed. When the average particle diameter is large, the glass powder may easily settle in forming a paste.

The maximum particle diameter of the glass powder is 100 μm or less. It is preferably 90 μm or less. Most preferably, it is 80 μm or less. When particle having particle diameter more than 100 μm are contained, operability may be poor and the glass powder may easily settle in forming a paste.

The softening point (Ts) of the glass powder (a) is preferably within a range of 500° C. to 650° C. By using the glass powder having a softening point (Ts) within the range of 500° C. to 650° C., it is possible to carry out firing at 650° C. to 850° C. and it is possible to apply to a core material which is prepared from a lithium disilicate base glass ceramics which includes a risk of deformation in firing more than 850° C.

The glass powder may be compounded in an appropriate amount so as to obtain a desired paste property, but the glass powder is compounded within a range of 50.0 to 80.0 wt. %, preferably 65.0 to 75.0 wt. %. When the compounding amount of the glass powder is too small, the uniform application property which is a feature of the present invention cannot be achieved and it tends to be difficult to maintain the paste property. When the compounding amount of the glass powder is too large, it tends to be difficult to form a paste.

The glass powder (a) used in the present invention is not particularly limited as long as it can be used in a dental porcelain, and may contain crystals. It is preferable that the softening point is less than 650° C. and firing is possible at a temperature of 650° C. to 850° C. Examples of the glass powder include a glass and a crystallized glass which contain $SiO_2$ as a main component (component having the largest content). Such glass may contain $Al_2O_3$, $B_2O_3$, ZnO, $K_2O$, $Na_2O$, $Li_2O$, $ZrO_2$, CaO, MgO and the like, in addition to $SiO_2$. Specific examples include amorphous type potassium aluminosilicate glass, amorphous type potassium borosilicate glass, crystal type potassium aluminosilicate glass, crystal type fluoroapatite glass and crystal type lithium silicate glass.

The glass powder (a) may also be partially or entirely treated with the silane coupling material shown below.

The average primary particle diameter of the hydrophobized fine particle silica (b) is within a range of 1 to 50 nm, preferably 5 to 45 nm, and more preferably 7 to 40 nm. When the average primary particle diameter of the hydrophobized fine particle silic is larger than 50 nm, a problem that it becomes difficult to maintain the paste property and improve the application property causes. Hydrophobized fine particle silica having an average primary particle diameter of less than 1 nm cannot be used because the preparation of such fine particle silica itself is difficult and uncommon. The hydrophobized fine particle silica is hydrophobized by a surface treatment.

The hydrophobized fine particle silica may be appropriately compounded according to the desired paste properties, but the compounding amount is within a range of 0.5 to 10 wt. %, preferably 2.0 to 5.0 wt. %. When the compounding amount of the hydrophobized fine particle silica is too small, there is a case in which it is difficult to maintain the paste property and improve the application property. Further, when the compounding amount of the hydrophobized fine particle silica is too large, there is a case in which cloudiness due to the hydrophobized fine particle silica may occur after firing.

The hydrophobized fine particle silica (b) is hydrophobized by a surface treatment with a surface treatment material. Examples of the surface treatment material include silane coupling materials and the like. Silane coupling materials are not limited in particular, but specific examples include methyl trimethoxy silane, dimethyl dimethoxy silane, phenyl trimethoxy silane, diphenyl dimethoxy silane, methyl triethoxy silane, dimethyl diethoxy silane, phenyl triethoxy silane, diphenyl diethoxy silane, isobutyl trimethoxy silane, vinyl trimethoxy silane, vinyl triethoxy silane, vinyl tris (2-methoxyethoxy) silane, 3,3,3-trifluoro propyl trimethoxy silane, methyl-3,3,3-trifluoro propyl dimethoxy silane, 2-(3, 4-epoxy cyclohexyl) ethyl trimethoxy silane, hexamethyl disilazane, 3-glycidoxypropyl trimethoxy silane, 3-glycidoxypropyl methyl diethoxy silane, 3-glycidoxypropyl triethoxy silane, 3-methacryloxy propyl methyl dimethoxy silane, polydimethyl siloxane, 3-methacryloxy propyl methyl diethoxy silane, N-2(aminoethyl) 3-aminopropyl methyl dimethoxy silane, N-2(aminoethyl) 3-aminopropyl trimethoxy silane, N-2(aminoethyl) 3-aminopropyl triethoxy silane, 3-aminopropyl trimethoxy silane, 3-aminopropyl triethoxy silane, N-phenyl-3-aminopropyl trimethoxy silane, 3-mercaptopropyl trimethoxy silane, trimethyl silanol, methyl trichloro silane, methyl dichloro silane, dimethyl dichloro silane, trimethyl chloro silane, phenyl trichloro silane, diphenyl dichloro silane, vinyl trichloro silane, trimethyl bromo silane, diethyl silane, vinyl triacetoxy silane, co-(meth) acryloxyalkyl trimethoxy silane (carbon number between (meth)acryloxy group and silicon atom: 3-12, example: 3-methacryloxy propyl trimethoxy silane, etc.), co-(meth) acryloxy alkyl triethoxy silane (carbon number between (meth)acryloxy group and silicon atom: 3-12, example: 3-methacryloxy propyl triethoxy silane, etc.) and the like.

Examples of the surface treatment method include a method of contacting the silane coupling material with the hydrophobized fine particle silica. Specific examples include a method which comprises putting the hydrophobized fine particle silica into a heated reactor, and pneumatically dispatching the silane coupling material in the reactor in parallel by an inert gas such as nitrogen at a ratio of 0.01 to 0.5 kg per 1 kg of silica.

In the present invention, silica other than the hydrophobized fine particle silica, for example, hydrophilic silica may be contained as long as the effect of the present invention is not affected. Specifically, in the present invention, the ratio of the silica other than the hydrophobized fine particle silica is preferably 50 wt. % or more and 100 wt. % or less, more preferably 60 wt. % or more and 100 wt. % or less, further preferably 70 wt. % or more 100 wt. %, more further preferably 80 wt. % or more and 100 wt. % or less, and most preferably 90 wt. % or more and 100 wt. % or less, of the total amount of silica. Further, in the present invention, it is preferable that no silica silica other than the hydrophobized fine particle silica is contained.

The organic solvent (c) having a boiling point of 100 to 300° C. is used as an essential component of the present invention. When the boiling point of the organic solvent is too low, the organic solvent volatilizes in the application and operability deteriorates. When the boiling point of the organic solvent is too high, unfired residue generates in firing, which causes carbonization and bubbles.

In the present invention, a paste can be formed by including the organic solvent within a range of 10.0 to 49.5 wt. % and it is possible to operate as the dental porcelain paste. The compounding amount is more preferably within a range of 25.0 to 35.0 wt. %. When the compounding amount of the organic solvent is too small, it becomes difficult to form a paste. When the compounding amount of the organic solvent is too large, separation from the glass powder due to aged deterioration easily occurs and carbonization and bubbles due to the organic component are caused after firing.

Specific examples of the organic solvent (c) used in the present invention include ester base solvents such as dimethyl phthalate and diethyl phthalate; polyhydric alcohol base solvents such as 1,2-butanediol, 1,3-butanediol, 1,4-butanediol, 1,5-pentanediol, glycerin, diethylene glycol, triethylene glycol, polyethylene glycol (molecular weight: 200 to 400), propylene glycol and dipropylene glycol; polyhydric alcohol monoether base solvents such as ethylene glycol monomethyl ether, ethylene glycol monoethyl ether, propylene glycol monomethyl ether, propylene glycol monoethyl ether, ethylene glycol monobutyl ether, diethylene glycol monomethyl ether, diethylene glycol monoethyl ether, propylene glycol monopropyl ether, tripropylene glycol monomethyl ether, diethylene glycol monobutyl ether and triethylene glycol monomethyl ether; and aromatic alcohol solvents such as 2-phenoxy ethanol and benzyl alcohol. Among these organic solvents, polyhydric alcohol base solvents, polyhydric alcohol monoether base solvents and aromatic alcohol solvents are preferable and 1,3-butanediol (boiling point: about 204° C.), propylene glycol (boiling point: about 189° C.) and 2-phenoxy ethanol (boiling point: about 240° C.) are more preferable. These organic solvents (c) can be used not only singly but also in appropriate combinations of two or more. When two or more kinds of organic solvents are used in combination, the total value obtained by multiplying the boiling points of the respective organic solvents to be used by the addition ratio is used as the boiling point of the organic solvents (c).

The dental porcelain paste of the present invention may contain a coloring material (d) and/or a fluorescent material (e).

The coloring material (d) is an inorganic material, and those commonly used in dental materials can be used. Specific examples include a coloring material prepared by mixing a plurality of metal oxides such as $SiO_2$, $Al_2O_3$, CaO, $TiO_2$, SnO, $Cr_2O_3$, MnO, $Sb_2O_3$, $V_2O_5$, ZnO, $Fe_2O_3$, $W_2O_3$, $Co_2O_3$ and $ZrO_2$, and firing. The compounding amount thereof is preferably within a range of 0.05 to 40 wt. %, more preferably 0.10 to 35 wt. %, and most preferably 0.30 to 30 wt. %.

The fluorescent material (e) is an inorganic material, and those commonly used in dental materials can be used. Specific examples include a fluorescent material prepared by mixing a plurality of metal oxides such as $SiO_2$, $Al_2O_3$, CaO, MgO, SrO, BaO, $Eu_2O_3$, $Y_2O_3$, $CeO_2$, $P_2O_5$, SnO, $Cr_2O_3$, MnO, $V_2O_5$, ZnO and $ZrO_2$, and firing. The compounding amount thereof is preferably within a range of 0.1 to 5.0 wt. %, more preferably 0.3 to 4.5 wt. %, and most preferably 0.5 to 4.0 wt. %. The coloring material (d) and/or the fluorescent material (e) are characterized by being an inorganic material.

The preparation of the dental porcelain paste of the present invention can be performed without limitation by the common preparation method of the paste composition held by a person skilled in the art. In an example of the general preparing method, the paste is prepared by compounding a glass powder, a hydrophobized fine particle silica, an organic solvent, a coloring material and a fluorescent material so that a target paste composition is obtained, and mixing with a stirring defoaming device.

EXAMPLES

Hereinafter, the present invention will be described in detail with reference to Examples and Comparative Examples. However, the present invention is not limited to the se Examples.

The evaluation method of a particle diameter and a softening point of glass powder, a primary particle diameter of hydrophobized fine particle silica, a flow value of paste composition, application property, a confirmation of bubbles and carbonization, and confirmation of paste separation, in Examples and Comparative Examples are described below.

(Measuring Method of Average Particle Diameter of Glass Powder)

The average particle diameter of the glass powder can be determined by measurement using a laser diffraction scattering method, a dynamic light scattering method, a centrifugal sedimentation method, an electrical sensing zone method, or the like. The particle diameters of the glass powders of Examples and Comparative Examples were measured by a laser diffraction scattering method. Specifically, the particle diameters were measured with a laser diffraction type particle size distribution measuring device Microtrac MT-3000II (manufactured by MicrotracBEL Corp).

(Measuring Method of Maximum Particle Diameter of Glass Powder)

The maximum particle diameter of the glass powder can be determined by measurement using a laser diffraction scattering method, a dynamic light scattering method, a centrifugal sedimentation method, an electrical sensing zone method, or the like. The particle diameters of the glass powders of Examples and Comparative Examples were measured by a laser diffraction scattering method. Specifically, the particle diameters were measured with a laser diffraction type particle size distribution measuring device Microtrac MT-3000II (manufactured by MicrotracBEL Corp).

(Measurement Method of Primary Particle Diameter of Hydrophobized Fine Particle Silica)

The primary particle diameter of the hydrophobized fine particle silica can be calculated from the specific surface area obtained by measurement using a gas absorption method, a mercury intrusion method, a gas permeation method, a bubble point method, or the like. The primary particle diameters of the hydrophobized fine particle silicas of the examples and comparative examples were measured by a gas absorption method. Specifically, the primary particle diameters were measured with micromeritics automatic surface area and porosimetry Analyzer, TriStar II 3020 (manufactured by Shimadzu Corporation).

(Measurement Method of Softening Point)

The softening point (Ts) of glass powder can be measured by the thermal expansion method. Specifically, the softening points of the glass powders of Examples and Comparative Examples were measured by the thermal expansion meter TM8140C (manufactured by Rigaku Corporation). In measurement, the glass powder was kneaded with the distilled water to prepare a kneaded material. The kneaded material was filled in a stick type mold made of the silicon (6×6×25 mm) and was subjected to condensation and water absorption repeatedly to prepare a molded body. The molded body was taken out from the silicon mold and was fired twice including one time vacuum firing and one time atmospheric firing by using the dental technique porcelain furnace "Esthemat Slim" (manufactured by Shofu Inc.). A test specimen was prepared by polishing both ends of the prepared twice fired product to prepare parallel faces and adjusting the size to 5×5×20 mm and measured.

(Preparation of Paste)

Glass powder, hydrophobized fine particle silica and organic solvent were mixed in a stirring and defoaming device so as to achieve the paste compositions (wt. %) described in Tables 1 and 2 to prepare pastes according to Examples 1 to 12 and Comparative examples 1 to 11.

(Evaluation of Flow Value)

The pastes of Examples and Comparative Examples were left to stand for 1 hour in a thermostatic chamber at 23° C. After leaving, the paste within a range of 0.3±0.03 g was measured and the measured paste was taken out and placed on a glass plate. One more glass plate was placed on the paste, and furthermore 20 g of a weight was placed thereon. After 30 seconds from placing the weight, the weight was removed. The longest diameter and the shortest diameter of the diameter of the circularity spread paste were measured and the average length of these was defined as the flow value. The rating criteria are as follows.

Less than 3 mm: Building-up was possible, and application was possible but with difficult.

3-20 mm: Both building-up and application were possible.

More than 20 mm: Application was possible, but building-up exceeding 0.1 mm thickness was not possible.

The pastes having flow values up to 20 mm were clinically usable.

(Preparation of Test Specimen)

The paste of each of the Examples and Comparative Examples was applied on the 10.0×10.0 mm surface of a zirconia plate (10.0×10.0×2.0 mm) to a thickness of 0.1 mm with a brush, and was vacuum fired at the temperature and time shown in Table 1 by using the dental technique porcelain furnace "Esthemat Slim" (manufactured by Shofu Inc.), and the fired product was used as a test specimen.

(Evaluation of Application Property)

The application property was evaluated at the time of preparing the test specimen. The evaluation criteria are shown below.

○: A uniform glass layer was prepared.

x: Not uniform and the zirconia surface was partially exposed.

(Confirmation of Bubbles and Carbonization)

The paste of each of the Examples and Comparative Examples was applied on a zirconia plate (10.0×10.0×2.0 mm) to a thickness of 1.0 mm, and was vacuum fired by using the dental technique porcelain furnace "Esthemat Slim" (manufactured by Shofu Inc.), and the fired product was used as a test specimen. The prepared test specimen was visually evaluated.

○: In a state of transparent glass layer.

x: Cloudiness due to generation of bubbles and blackening due to carbonization occurred.

(Confirmation of Paste Separation)

The paste of 3 g of each of the pastes of Examples and Comparative Examples was weighed and the weighed paste was placed into a glass bottle of 5 ml. After closing with a lid, the bottle was placed in a thermostat set at 50° C. and was allowed to stand for 7 days. Thereafter, the paste in the glass bottle taken out from the thermostat used as a test specimen. The storage stability of this test sample was visually evaluated.

○: Almost no change from the state after mixing.

x: The liquid and powder were separated, for example, the organic solvent floated on the surface or the glass powder settled at the bottom.

Examples 1 to 22, Comparative Examples 1 to 16

Compositions Used in Examples and Comparative Examples

Glass powders consisted of $SiO_2$, $Al_2O_3$, $K_2O$ and other components, and glass powders having the average particle diameter of 0.5 μm, 1 μm, 5 μm, 20 μm, and 26 μm were prepared by crushing aluminosilicate glass having a softening point (Ts) of 575° C. by a common crushing machine and used.

RX50, R974, R812, #50, #200, #300 (manufactured by Nippon Aerosil Co., Ltd.), YA050C, YA100C (manufactured by Admatechs.) were used as the hydrophobized fine particle silica and the hydrophilic fine particle silica.

As the organic solvent, ethanol (bp=89° C.), propylene glycol (bp=188.2° C.), 1,3-butanediol (bp=204° C.), and benzyl benzoate (bp=324° C.) were used.

TABLE 1

| | Paste composition (wt. %) | | | | | | | | | | | | | | | |
|---|---|---|---|---|---|---|---|---|---|---|---|---|---|---|---|---|
| | Glass powder (Ts = 575° C.) | | | | | | | | Hydrophobized fine particle silica | | | | | Hydrophilic fine particle silica | | |
| | Glass Powder 0.5 µm | Glass Powder 1 µm | Glass Powder 2 µm | Glass Powder 5 µm | Glass Powder 10 µm | Glass Powder 20 µm | Glass Powder 26 µm | Maximum particle diameter (µm) | R812 Average primary particle diameter 7 nm | R974 Average primary particle diameter 12 nm | RX50 Average primary particle diameter 40 nm | YA050C Average primary particle diameter 50 nm | YA100C Average primary particle diameter 100 nm | #50 Average primary particle diameter 7 nm | #200 Average primary particle diameter 12 nm | #300 Average primary particle diameter 40 nm |
| Example 1 | | 70 | | | | | | 52 | | 3 | | | | | | |
| Example 2 | | | | 70 | | | | 62 | | 3 | | | | | | |
| Example 3 | | | | | | 70 | | 88 | | 3 | | | | | | |
| Example 4 | | 50 | | | | | | 52 | | 10 | | | | | | |
| Example 5 | | 65 | | | | | | 52 | | 5 | | | | | | |
| Example 6 | | | | 73 | | | | 62 | | 2 | | | | | | |
| Example 7 | | | | | | 80 | | 88 | | 0.5 | | | | | | |
| Example 8 | | | | 70 | | | | 62 | | 3 | | | | | | |
| Example 9 | | | | 70 | | | | 62 | 3 | | | | | | | |
| Example 10 | | | | 70 | | | | 62 | | | 3 | | | | | |
| Example 11 | | | | 70 | | | | 62 | | 3 | | | | | | |
| Example 12 | | | | 80 | | | | 62 | | 10 | | | | | | |
| Example 13 | | | | 70 | | | | 62 | | 2 | 1 | | | | | |
| Example 14 | | | | 70 | | | | 62 | 1 | 2 | | | | | | |
| Example 15 | | | | 70 | | | | 62 | 1 | 1 | 1 | | | | | |
| Example 16 | | | 70 | | | | | 55 | | 3 | | | | | | |
| Example 17 | | | | | 70 | | | 70 | | 3 | | | | | | |
| Example 18 | | | | 70 | | | | 62 | | | | 3 | | | | |
| Example 19 | | | | 70 | | | | 62 | | 2 | | | | 1 | | |
| Example 20 | | 50 | | | | | | 52 | | 0.5 | | | | | | |
| Example 21 | | | | 65 | | | | 62 | | 3 | | | | | | |
| Example 22 | | | | 67 | | | | 62 | | 3 | | | | | | |

| | Paste composition (wt. %) | | | | | | | | |
|---|---|---|---|---|---|---|---|---|---|
| | Organic solvent | | | | | | | | |
| | Eethanol bp = 89° C. | Propylene glycol bp = 188.2° C. | 1,3-butanediol bp = 204° C. | Benzyl benzoate bp = 324° C. | Inorganic pigment | Fluorescent material | Firing temparature | Firing period | Total |
| Example 1 | | | 27 | | | | 750 | 1 | 100 |
| Example 2 | | | 27 | | | | 750 | 1 | 100 |

TABLE 1-continued

| | | | | | | | |
|---|---|---|---|---|---|---|---|
| Example 3 | | 27 | | | 750 | 1 | 100 |
| Example 4 | | 40 | | | 750 | 1 | 100 |
| Example 5 | | 30 | | | 750 | 1 | 100 |
| Example 6 | | 25 | | | 750 | 1 | 100 |
| Example 7 | | 19.5 | | | 750 | 1 | 100 |
| Example 8 | 27 | | | | 750 | 1 | 100 |
| Example 9 | | 27 | | | 750 | 1 | 100 |
| Example 10 | | 27 | | | 750 | 1 | 100 |
| Example 11 | 13 | 14 | | | 750 | 1 | 100 |
| Example 12 | 10 | | | | 750 | 1 | 100 |
| Example 13 | | 27 | | | 750 | 1 | 100 |
| Example 14 | | 27 | | | 750 | 1 | 100 |
| Example 15 | | 27 | | | 750 | 1 | 100 |
| Example 16 | | 27 | | | 750 | 1 | 100 |
| Example 17 | | 27 | | | 750 | 1 | 100 |
| Example 18 | | 27 | | | 750 | 1 | 100 |
| Example 19 | | 27 | | | 750 | 1 | 100 |
| Example 20 | | 49.5 | | | 750 | 1 | 100 |
| Example 21 | | 27 | 5 | | 750 | 1 | 100 |
| Example 22 | | 27 | | 3 | 750 | 1 | 100 |

TABLE 2

| | Paste composition (wt. %) | | | | | | | | | | | | | | | |
|---|---|---|---|---|---|---|---|---|---|---|---|---|---|---|---|---|
| | Glass powder (Ts = 575° C.) | | | | | | | | Hydrophobized fine particle silica | | | | | Hydrophilic fine particle silica | | |
| | Glass Powder 0.5 μm | Glass Powder 1 μm | Glass Powder 2 μm | Glass Powder 5 μm | Glass Powder 10 μm | Glass Powder 20 μm | Glass Powder 26 μm | Maximum particle diameter (μm) | R812 Average primary particle diameter 7 nm | R974 Average primary particle diameter 12 nm | RX50 Average primary particle diameter 40 nm | YA050C Average primary particle diameter 50 nm | YA100C Average primary particle diameter 100 nm | #50 Average primary particle diameter 7 nm | #200 Average primary particle diameter 12 nm | #300 Average primary particle diameter 40 nm |
| Comparative Example 1 | 70 | | | | | | | 49 | | 3 | | | | | | |
| Comparative Example 2 | | | | | | | 70 | 113 | | 3 | | | | | | |
| Comparative Example 3 | | 70 | | | | | | 52 | | | | | | 3 | | |

TABLE 2-continued

| | | | | | | | | | | | |
|---|---|---|---|---|---|---|---|---|---|---|---|
| Comparative Example 4 | | | | 70 | | 88 | | | | 3 | |
| Comparative Example 5 | | 70 | | | | 52 | | | | | 3 |
| Comparative Example 6 | | 70 | | | | 52 | 3 | | | | |
| Comparative Example 7 | | | | 70 | | 88 | 3 | | | | |
| Comparative Example 8 | | | 85 | | | 62 | 2 | | | | |
| Comparative Example 9 | | | 45 | | | 62 | 10 | | | | |
| Comparative Example 10 | | | 70 | | | 62 | | | | | |
| Comparative Example 11 | | | 50 | | | 62 | 13 | | | | |
| Comparative Example 12 | | | 90 | | | 62 | 3 | | | | |
| Comparative Example 13 | | | 40 | | | 62 | 10 | | | | |
| Comparative Example 14 | | | | | 70 | 113 | | | 3 | | |
| Comparative Example 15 | 70 | | | | | 49 | | | | | 3 |
| Comparative Example 16 | | | 70 | | | 62 | | 3 | | | |

TABLE 2-continued

| | Paste composition (wt. %) | | | | | | | | |
|---|---|---|---|---|---|---|---|---|---|
| | Organic solvent | | | | | | | | |
| | Eethanol bp = 89° C. | Propylene glycol bp = 188.2° C. | 1,3-butanediol bp = 204° C. | Benzyl benzoate bp = 324° C. | Inorganic pigment | Fluorescent material | Firing temparature | Firing period | Total |
| Comparative Example 1 | | | 27 | | | | 750 | 1 | 100 |
| Comparative Example 2 | | | 27 | | | | 750 | 1 | 100 |
| Comparative Example 3 | | | 27 | | | | 750 | 1 | 100 |
| Comparative Example 4 | | | 27 | | | | 750 | 1 | 100 |
| Comparative Example 5 | | | 27 | | | | 750 | 1 | 100 |
| Comparative Example 6 | 27 | | | | | | 750 | 1 | 100 |
| Comparative Example 7 | | | | 27 | | | 750 | 1 | 100 |
| Comparative Example 8 | | | 13 | | | | 750 | 1 | 100 |
| Comparative Example 9 | | 45 | | | | | 750 | 1 | 100 |
| Comparative Example 10 | | | 30 | | | | 750 | 1 | 100 |
| Comparative Example 11 | | | 37 | | | | 750 | 1 | 100 |
| Comparative Example 12 | | 7 | | | | | 750 | 1 | 100 |
| Comparative Example 13 | | | 50 | | | | 750 | 1 | 100 |

TABLE 2-continued

| | | | | | | |
|---|---|---|---|---|---|---|
| Comparative Example 14 | | | 27 | 750 | 1 | 100 |
| Comparative Example 15 | 27 | | | 750 | 1 | 100 |
| Comparative Example 16 | | 27 | | 750 | 1 | 100 |

TABLE 3

| | Result | | | |
|---|---|---|---|---|
| | Flow value (mm) | Application property | Bubbles and Carbonization | Paste separation |
| Example 1 | 5 | ○ | ○ | ○ |
| Example 2 | 7 | ○ | ○ | ○ |
| Example 3 | 12 | ○ | ○ | ○ |
| Example 4 | 0 | ○ | ○ | ○ |
| Example 5 | 5 | ○ | ○ | ○ |
| Example 6 | 9 | ○ | ○ | ○ |
| Example 7 | 1 | ○ | ○ | ○ |
| Example 8 | 7 | ○ | ○ | ○ |
| Example 9 | 6 | ○ | ○ | ○ |
| Example 10 | 6 | ○ | ○ | ○ |
| Example 11 | 6 | ○ | ○ | ○ |
| Example 12 | 0 | ○ | ○ | ○ |
| Example 13 | 6 | ○ | ○ | ○ |
| Example 14 | 5 | ○ | ○ | ○ |
| Example 15 | 6 | ○ | ○ | ○ |
| Example 16 | 6 | ○ | ○ | ○ |
| Example 17 | 10 | ○ | ○ | ○ |
| Example 18 | 16 | ○ | ○ | ○ |
| Example 19 | 8 | ○ | ○ | ○ |
| Example 20 | 19 | ○ | ○ | ○ |
| Example 21 | 7 | ○ | ○ | ○ |
| Example 22 | 7 | ○ | ○ | ○ |
| Comparative Example 1 | 6 | x Uneven | ○ | ○ |
| Comparative Example 2 | 7 | x Uneven | ○ | x Separation |
| Comparative Example 3 | 9 | x Uneven | ○ | x Separation |
| Comparative Example 4 | 9 | x Uneven | ○ | x Separation |
| Comparative Example 5 | 10 | x Uneven | ○ | x Separation |
| Comparative Example 6 | 18 | x Uneven | ○ | x Separation |
| Comparative Example 7 | 2 | ○ | x Carbonization | ○ |
| Comparative Example 8 | Impossible to make uniform paste | | | |
| Comparative Example 9 | 9 | x Uneven | ○ | ○ |
| Comparative Example 10 | 1 | x Uneven | ○ | x Separation |
| Comparative Example 11 | ○ | ○ | x Bubbles | ○ |
| Comparative Example 12 | Impossible to make uniform paste | | | |
| Comparative Example 13 | 11 | x Uneven | ○ | x Separation |
| Comparative Example 14 | 10 | x Uneven | ○ | ○ |
| Comparative Example 15 | 21 | ○ | ○ | x Separation |
| Comparative Example 16 | 15 | x Uneven | ○ | x Separation |

In all of the examples, excellent application property was exhibited, and the samples after firing were transparent and exhibited excellent storage stability.

On the other hand, in Comparative Examples 1-6, 9-10, 13-14 and 16, excellent application property was not exhibited because the surface after firing was a non-uniform surface. In Comparative Examples 7 and 11, blackening due to carbonization or cloudiness due to air bubbles was confirmed after firing, and therefore transparency after firing was not obtained. In Comparative Examples 2-6, 10, 13, and 15-16, excellent storage stability was not obtained because the paste separated in the storage stability test. For Comparative Examples 8 and 12, a uniform paste was not prepared.

From the above results, the dental porcelain paste of the present invention showed good results including excellent application property, transparent after firing, and satisfaction of the storage stability of the paste due to aged deterioration. It is considered that this is due to the fact that the paste is formed by combining the glass powder containing the hydrophobized fine particle silica hydrophobized by the surface treatment and having a controlled particle diameter with a suitable organic solvent.

Therefore, the dental porcelain paste of the present invention dramatically improves the application property, transparency, and the storage stability which can maintain the paste property for a long period of time in the conventional paste composition.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

INDUSTRIAL AVAILABILITY

The dental porcelain paste provided by the present invention can maintain a paste state for a long period of time, has excellent application property, and hardly causes carbonization or bubbles due to the influence of an organic component or a polymer component during firing, and therefore can be applied to various restorations of the crown in restoration treatment in the dental field.

What is claimed is:

1. A dental porcelain paste for preparing a dental prosthesis device, comprising:

50.0 to 80.0 wt. % of a glass powder (a) having a maximum particle diameter of 100 μm or less and an average particle diameter of 1 to 20 μm, 0.5 to 10.0 wt. % of a hydrophobized fine particle silica (b) having an average primary particle diameter of 1 to 50 nm, and 10.0 to 49.5 wt. % of an organic solvent (c) having a boiling point (bp) of 100 to 300° C.

2. The dental porcelain paste according to claim 1, further comprising:

a coloring material (d) and/or a fluorescent material (e).

* * * * *